United States Patent [19]

Kendall

[11] Patent Number: 5,190,834
[45] Date of Patent: Mar. 2, 1993

[54] COMPOSITE MEMBRARNES AND ELECTROCHEMICAL CELLS CONTAINING THEM

[75] Inventor: Kevin Kendall, Runcorn, England

[73] Assignee: Imperial Chemical Industries PLC, London, England

[21] Appl. No.: 780,204

[22] Filed: Oct. 22, 1991

[30] Foreign Application Priority Data

Oct. 24, 1990 [GB] United Kingdom ............... 9023091

[51] Int. Cl.$^5$ ........................................... H01M 6/18
[52] U.S. Cl. .................................... 429/31; 429/193; 29/623.1
[58] Field of Search ................... 429/30–33, 429/193, 34; 29/623.1; 427/115; 419/1, 38, 65, 66

[56] References Cited

U.S. PATENT DOCUMENTS 3,402,230  9/1968  White, Jr. ...................... 429/31 X
3,525,646  8/1970  Tannenberger .................... 429/31
4,666,798  5/1987  Herceg ........................... 429/30 X
4,761,349  8/1988  McPheeters ........................ 429/30
5,045,169  9/1991  Feduska et al. .................. 429/31 X
5,051,321  9/1991  Kitagawa et al. ................... 429/30
5,059,497  10/1991 Prince ............................ 429/30

Primary Examiner—Anthony Skapars
Attorney, Agent, or Firm—Cushman, Darby & Cushman

[57] ABSTRACT

A composite membrane comprising one or more domains of an electrolyte material and one or more domains of an electronically conducting interconnect material, said electrolyte domain(s) and said interconnect domain(s) traversing the thickness of the membrane so that the membrane comprises contact surfaces for the or each electrolyte domain and the or each interconnect domain on both major faces thereof. Also claimed is an electrochemical cell comprising the composite membrane and having one or more anodes arranged on one major face and one or more cathodes arranged on the other major face of the membrane.

15 Claims, 2 Drawing Sheets

COMPOSITE MEMBRARNES AND ELECTROCHEMICAL CELLS CONTAINING THEM

The present invention relates to composite membranes, processes for the fabrication of the composite membranes, electrochemical cells comprising the membranes and processes for the fabrication of the electrochemical cells. In particular, the present invention relates to electrochemical cells for use in solid oxide fuel cell assemblies.

Solid oxide fuel cells, hereinafter referred to as SOFC's, are well known in the art and are described, for example, in the Journal of Power Sources, Volume 29 (1990), pp 223-237. The existing designs for SOFC's are based on tubular, planar or monolithic concepts and are complex and expensive to produce.

One particular problem which the present invention sets out to solve is, therefore, to provide a SOFC of simplified construction and lower cost.

According to the first aspect of the present invention there is provided a composite membrane comprising one or more domains of an electrolyte material and one or more domains of an electronically conducting interconnect material, said electrolyte domain(s) and said interconnect domain(s) traversing the thickness of the membrane so that the membrane comprises contact surfaces for the or each electrolyte domain and the or each interconnect domain on both major faces thereof.

According to the second aspect of the present invention there is provided an electrochemical cell comprising:
(a) at least one composite membrane having one or more domains of an electrolyte material and one or more domains of an electronically conducting interconnect material, which domains traverse the thickness of the membrane;
(b) one or more anodes arranged on one major face of the or each composite membrane; and
(c) one or more cathodes arranged on the other major face of the or each composite membrane, the arrangement of the components in the cell being such that the or each electrolyte domain and the or each interconnect domain make contact with both an anode and a cathode, and the or each anode and the or each cathode make contact with both an electrolyte domain and an interconnect domain.

The electrolyte material is an ion conductor, and normally forms a substantial proportion of the total area of the composite membrane. Clearly, the anode(s) and cathode(s) are also electronic conductors.

In the electrochemical cell, the anode(s) and cathode(s) are respectively positioned on opposite major faces of the or each membrane and contact both an interconnect domain and an electrolyte domain. The interconnect domain(s) provides for the conduction of electricity between the anode(s) and cathode(s), and the electrolyte domain(s) provides for the transport of ions across the membrane between the anode(s) and cathode(s). In one preferred embodiment, the composite membrane will comprise a plurality of electrolyte domains and a plurality of interconnect domains which adjoin one another, and the electrochemical cell comprising such a membrane(s) will preferably comprise a plurality of anodes and a plurality of cathodes respectively arranged on opposite major faces of the membrane(s), with each anode and each cathode making contact with an electrolyte domain and an interconnect domain, and each electrolyte domain and each interconnect domain making contact with an anode and a cathode.

The electrochemical cell may comprise a plurality of electrolyte/interconnect composite membranes each having one or more anodes arranged on one major face thereof and one or more cathodes arranged on the other major face thereof. With such an electrochemical cell, it is not necessary for an interconnect domain of a particular membrane to contact both an anode and a cathode positioned on that membrane. For example, an interconnect domain of one membrane may contact a cathode positioned on that membrane and an anode positioned on an adjacent membrane. Alternatively, an interconnect domain of one membrane may contact an anode positioned on that membrane and a cathode positioned on an adjacent membrane.

The composite membrane of the invention may be substantially planar, or it may have a more complex non-planar form, for example a corrugated or a spiral shape. A further useful composite membrane has a tubular shape. With a tubular membrane the inner and outer surfaces thereof constitute the major faces of the membrane on which the electrode components can be arranged. The electrochemical cells of the invention may similarly have a substantially planar, corrugated, spiral or tubular shape.

In a preferred embodiment, the composite membrane comprises a plurality of essentially parallel striations or stripes of interconnect material which are contiguous with essentially parallel bands of electrolyte material. Such a membrane comprises an alternating arrangement of essentially parallel interconnect striations and electrolyte bands which extend between opposing edges of the membrane. The stripes of interconnect material need not, necessarily, be continuous along their length, e.g. they may be traversed by the electrolyte material so that the interconnect stripes have the form of broken lines. An electrochemical cell comprising such a membrane(s) will preferably comprise essentially parallel bands of anodic electrode material arranged on one major face of the membrane, and essentially parallel bands of cathodic electrode material on the opposing major face thereof. The width of each anode band will be such that it overlaps an interconnect striation and the electrolyte band on one or both sides thereof. The width of the cathodic electrode bands will also be similarly governed. The electrode bands may be continuous or discontinuous, but are preferably continuous.

Suitable materials for the fabrication of the electrolyte/interconnect membrane and the electrode components are the solid inorganic materials which possess the requisite properties to function as an electrolyte, an interconnect or an electrode. Such materials include, inter alia, metals, metal alloys, ceramics and ceramic/metallic materials (cermets). Ceramics and cermets are especially preferred materials for the fabrication of the membranes and electrochemical cells of the invention. Preferably, the thermal expansion coefficients of the components of the electrochemical cell do not differ by more than 10%, so as to reduce the risk of delamination or cracking when the cell is in use.

The composite membranes of the invention are conveniently fabricated from particulate electrolyte and interconnect materials which can be formed into an integral mass by sintering, i.e. by the application of heat and, optionally, pressure. The particulate electrolyte and interconnect materials can be separately agglomerated into sinterable masses by dispersion in a binder comprising an organic polymer in solution or dispersion in a liquid vehicle, so as to form a coherent, dough-like composition having sufficient deformability to allow for the shaping thereof. Polymer doughs separately containing the particulate electrolyte material and the particulate interconnect material can be shaped and assembled into a dough layer which is then formed into a thin cohesive sheet (precursor membrane), e.g. by rolling, pressing or extrusion. The precursor membrane comprises one or more domains of the particulate electrolyte material and one or more domains of the particulate interconnect material bound together by the polymeric binder. The liquid vehicle can be actively or passively removed from the precursor membrane by evaporation and the polymer burned-out prior to effecting sintering of the particulate masses to form the composite membrane. It will be appreciated that the dough layer may comprise many separate pieces of suitably shaped dough material comprising respectively particles of electrolyte material and particles of interconnect material.

For example, to form a composite membrane having an alternating arrangement of essentially parallel interconnect striations and electrolyte bands, strips of a deformable dough comprising dispersed particles of an electrolyte material can be laid up between strips of a deformable dough comprising dispersed particles of an interconnect material, to form a dough layer comprising alternating strips of the two dough materials. The strips of dough may be produced directly by a rolling, pressing or extrusion processes or they may be cut from a moulded sheet of the dough which has been produced using such processes. At this stage the dough layer may be pressed from the sides to loosely knit the strips together. The dough layer can then be rolled, pressed or otherwise moulded to untie the strips into a thin cohesive sheet which constitutes the precursor membrane. The so formed precursor membrane can then be treated as described above to form the composite membrane.

The fabrication of a composite membrane using the above described techniques is particularly desirable, since the polymer containing precursor membrane tends to possess a degree of inherent flexibility which allows it to be wrapped around formers, e.g. fibrous ceramic boards, to produce non-planar shapes, for example a corrugated shape, a spiral or a tube. The burning-out and sintering operations tend to fix the composite membrane in the required shape, allowing for removal of the formers, if desired. This property allows a large area of the composite membrane to be stored in a compact space, so that apparatus comprising the membrane can be made less cumbersome. Of course, we do not exclude the possibility that the composite membrane itself may possess sufficient flexibility to enable it to be arranged into a corrugated, spiral or other non-planar shape.

Alternatively, polymer doughs separately containing the particulate electrolyte and particulate interconnect materials can be shaped and assembled into a block, e.g. a cylindrical block, which is then extruded through a die to yield a tubular precursor membrane comprising one or more domains of particulate electrolyte material and one or more domains of particulate interconnect material bound together by the polymeric binder. Removal of the liquid medium, burning out of the polymer and sintering yields a tubular shaped composite membrane. Extrusion techniques for making tubes are known in the art and can be applied to the manufacture of tubular composite membranes.

A preferred tubular composite membrane comprises one or more bands of electrolyte material and one or more striations or stripes of interconnect material which are contiguous with one another and extend along the length of the tube from one end thereof to the other. A tubular membrane of this type can be prepared by extrusion of a cylindrical block constructed from the interconnect and electrolyte containing polymer doughs by arranging the interconnect polymer dough in one or more segments which run along the length of the cylindrical block. The stripes of interconnect need not, necessarily, be continuous along their length, e.g. they may be traversed by the electrolyte material so that the interconnect stripes have the form of broken lines.

An electrochemical cell comprising a tubular composite membrane(s) will have the anode(s) arranged on one of either the inner or outer surface of the tubular membrane, and the cathode(s) arranged on the other of either the inner or outer surface of the tubular membrane.

Burning-out of the polymer may be effected by progressively increasing the temperature of the dried precursor membrane (i.e. after removal of the liquid vehicle). The temperature should not be increased at a rate which results in such a rapid burn-out of the organic polymeric material that the structural integrity of the membrane is disturbed. Increasing the temperature at a rate of 1° C./minute up to a maximum temperature of 500° C. is usually suitable for burning-out the polymeric material.

Sintering of the particulate masses is achieved by heating to high temperatures, optionally with the application of pressure. The sintering temperature will, of course, depend on the nature of the particulate material, but normally temperatures in excess of 500° C., e.g. 1200° C. or higher, are employed.

The thickness of the composite membrane will typically be in the range 50 to 500 microns, e.g. 50 to 150 microns. Where the composite membrane comprises alternating electrolyte bands and interconnect striations, the width thereof will depend on the areal extent of the membrane, though a width in the range 2 to 30 mm, e.g. 3 to 20 mm, is convenient for the electrolyte bands, while the interconnect striations are conveniently less than 1 mm wide, e.g. less than 0.2 mm wide.

The electrodes may be laid down at any stage during the fabrication of the composite membrane. Various techniques are available for the application of the electrode components, though particular mention should be made of the coating techniques known in the art such as spraying, brushing, roller coating, tape rolling and screen printing, all of which employ particulate dispersions of the electrode material in a suitable liquid vehicle and deposit thin layers of electrode material. Masking techniques may be employed to ensure that, in the final electrochemical cell, the electrodes cover the required areas of the composite membrane. Where the electrode material is deposited using coating techniques, it will be necessary, after deposition, to actively or passively remove the liquid vehicle, which removal may require a burning-out step where the vehicle comprises a polymeric material. The so deposited electrode material may then be subjected to a sintering process.

While the electrode material may be coated onto a preformed composite membrane, the necessity to remove the liquid vehicle and to employ a sintering step, may make such an approach economically undesirable when the membrane is itself made using the dough moulding technology discussed supra. Furthermore, the application of electrode components to composite membranes which have a complex non-planar shape may prove difficult. Accordingly, in such cases, it may be convenient to coat the electrode material onto the precursor membrane to form a precursor cell, which is then processed by solvent evaporation, burning-out and sintering to form the electrochemical cell.

In a preferred embodiment, the electrodes are applied to the membrane using a modification of the dough moulding process discussed supra for the fabrication of the membrane. Thus, suitably shaped pieces of deformable dough separately containing the particulate anodic and cathodic electrode materials can be laid down on each face of the dough layer prepared as described above. The anode containing dough material is laid down on one face of the dough layer, and the cathode containing dough material on the other. The resulting dough tri-layer is then formed into a precursor cell comprising a precursor membrane with a precursor anodic electrode(s) formed on one major face and a precursor cathodic electrode(s) formed on the other major face of the precursor membrane, e.g. by rolling, pressing or extrusion. Where the dough tri-layer comprises a plurality of anode containing dough pieces on one face thereof and a plurality of cathode containing dough pieces on the other face thereof, compressible spacers may be placed between the dough pieces of anodic and cathodic electrode material to ensure that the precursor electrodes in the resulting precursor cell do not contact each other. Removal of the liquid vehicle, burning out of the polymeric material and sintering of the particulate materials converts the precursor cell into an electrochemical cell of the invention.

The precursor cell may be formed into non-planar shapes in the same way as described above for the precursor membrane.

The electrodes typically have a thickness in the range 20 to 100 microns. For an electrochemical cell comprising a composite membrane(s) having essentially parallel interconnect striations and electrolyte bands, and essentially parallel anode bands on one major face of the membrane and essentially parallel cathode bands on the other major face of the membrane, the width of the electrode bands will depend on the width of the electrolyte bands and interconnect striations, bearing in mind that a given electrode should contact both an interconnect striation and an electrolyte band.

Where the electrochemical cell is fabricated from a precursor cell, it is preferred that the burning out and sintering shrinkage of the various components of the precursor cell should not differ by more than 5%. Differences in shrinkage of greater than 5% may lead to delamination and cracking during the burning-out and/or sintering operations.

In use, the electrochemical cell will be provided with terminal connectors which transfer current to or collect current from the electrodes. Suitable materials for the formation of the terminal connectors are the materials having good conductivity (i.e. low resistivity) such as metals, metal alloys and cermets. Especially preferred materials are the cermets due to their resistance to reactive chemical environments and high temperatures.

The electrochemical cell of the invention is particularly suitable for use in SOFC assemblies. SOFC's are electrochemical systems that convert the chemical energy of the reactants into electrical energy. The SOFC operates at approximately 1000° C., burning fuel at the anode and consuming an oxidant at the cathode. In a SOFC assembly a gaseous fuel, e.g. hydrogen or a hydrogcarbon such as methane, is caused to flow over the anode face of the electrochemical cell, and an oxidant gas, which is usually oxygen, but may be air, is caused to flow over the cathode face of the electrochemical cell. Mobile $O^{2-}$ ions travel across the electrolyte from the cathode (air electrode) to the anode (fuel electrode) and arrive at the electrolyte/anode interface where they react with the gaseous fuel within the porous anode.

When the electrochemical cell is to be used in a SOFC assembly, the electrolyte should be impervious to the fuel and oxidant gases and should be chemically resistant to those gases, and the reactive environment which prevails, during operation of the SOFC. The electrolyte should also be conductive to $O^{2-}$ ions. Suitable materials for the electrolyte may be selected from the inorganic oxides, in particular the ceramic oxides such as hafnia ($HfO_2$), yttria ($Y_2O_3$), zirconia ($ZrO_2$) and yttria, ceria or rare earth stabilised zirconia, the latter materials optionally including a proportion of indium oxide ($In_2O_3$) or praseodymia ($Pr_2O_3$). Particularly preferred materials are zirconia and especially yttria stabilised zirconia. A preferred electrolyte has a density which is at least 90%, e.g. 95%, of the theoretical density of the material of which it is composed, and a closed porosity amounting to less than 10 volume %, e.g. 5 volume %.

When the electrochemical cell is to be used in a SOFC assembly, the interconnect should be impervious to the fuel and oxidant gases and should be chemically resistant to those gases, and the reactive environment which prevails, during operation of the SOFC. The interconnect should also be an electronic conductor. Suitable materials for the interconnect may be selected from the perovskite ceramics having the general formula $ABO_3$, where A is, for example, La or Pb and B is, for example, Cr, Co, Zr or Ti, optionally doped with alkaline earth metals such as Sr, Mg or Ca. Another suitable material for the interconnect may be Nb doped titanium glass composite. Preferred materials for the interconnect are lanthanum cobaltite ($LaCoO_3$), lanthanum chromite ($LaCrO_3$) and especially alkaline earth metal doped lanthanum chromite. A preferred interconnect has a density which is at least 90%, e.g. 95%, of the theoretical density of the material of which it is composed, and a closed porosity amounting to less than 10 volume %, e.g. 5 volume %.

When the electrochemical cell is to be used in a SOFC assembly, the anode or fuel electrode should be stable to the fuel, and the reactive environment which prevails, during operation of the SOFC. Suitable materials for the anode may be selected from the porous metals such as Ni, and especially the porous cermets, particularly cermets of Ni and an inert phase such as zirconia or yttria stabilised zirconia. Other suitable anode materials may be selected from $PrInO_3$, $Hf_2In_2O_7$ or a solid solution of indium oxide ($In_2O_3$) containing hafnia, praseodymium dioxide ($PrO_2$) or $PrO_{1.83}$. Preferred materials are zirconia nickel cermets and yttria stabilised zirconia nickel cermets, especially the latter. The nickel may be added as nickel oxide which is reduced to the metal in the reducing fuel atmosphere as the SOFC is heated. A preferred anode has a density which is less than 80%, e.g. 70%, of the theoretical density of the material of which it is composed, and an open porosity amounting to more than 20 volume %, e.g. 30 volume %.

When the electrochemical cell is to be used in a SOFC assembly, the cathode or air electrode should be resistant to oxidation by the oxidant gas (air or oxygen), and the reactive environment which prevails, during operation of the SOFC. The cathode must permit rapid diffusion of the air or oxygen to the electrolyte/anode interface. A suitable material for the cathode is a Sr doped lanthanum manganite perovskite. A preferred cathode has a density which is less than the material of which it is composed, and an open porosity amounting to more than 20 volume %, e.g. 30 volume %.

The required porosity and density of the components forming the electrochemical cell may be achieved using the dough moulding technology discussed supra, by exercising control over the amount and particle size of the particulate material which is incorporated in the dough. The higher the proportion of particulate material in the dough and the smaller the particle size thereof, the higher will be the density and the lower will be the porosity of the final sintered product. Exercising control over the amount of polymeric material in the dough will also affect the degree of porosity of the final sintered product, since its presence tends to assist pore formation. The sintering temperatures employed will also have a bearing on the final density and porosity of the product, higher temperatures leading to denser products of lower porosity. Obtaining products of the required density and porosity is within the purview of the ceramicist.

The assembly of the electrochemical cell of the invention into a SOFC device is within the purview of the man skilled in the art. Typically, a SOFC will comprise a plurality of the electrochemical cells described above. Manifolds may be used to support the electrochemical cells in the appropriate configuration and electrical connections will need to be provided between the cells in order to form an electrically integrated system. The SOFC will of course comprise suitable means for conveying the oxidant and fuel to the appropriate electrodes and means for collecting the electrical current generated in the electrochemical cells.

It will, of course, be appreciated that the electrochemical cell of the invention may be usefully employed in fuel cells other than the SOFC type. Another possible application for the electrochemical cell of the invention is in an electrolytic cell for the conversion of reactants to products by means of an electromotive force supplied to the electrodes.

Particular embodiments of the present invention will now be described with reference to the accompanying drawings, in which.

Figure 1:
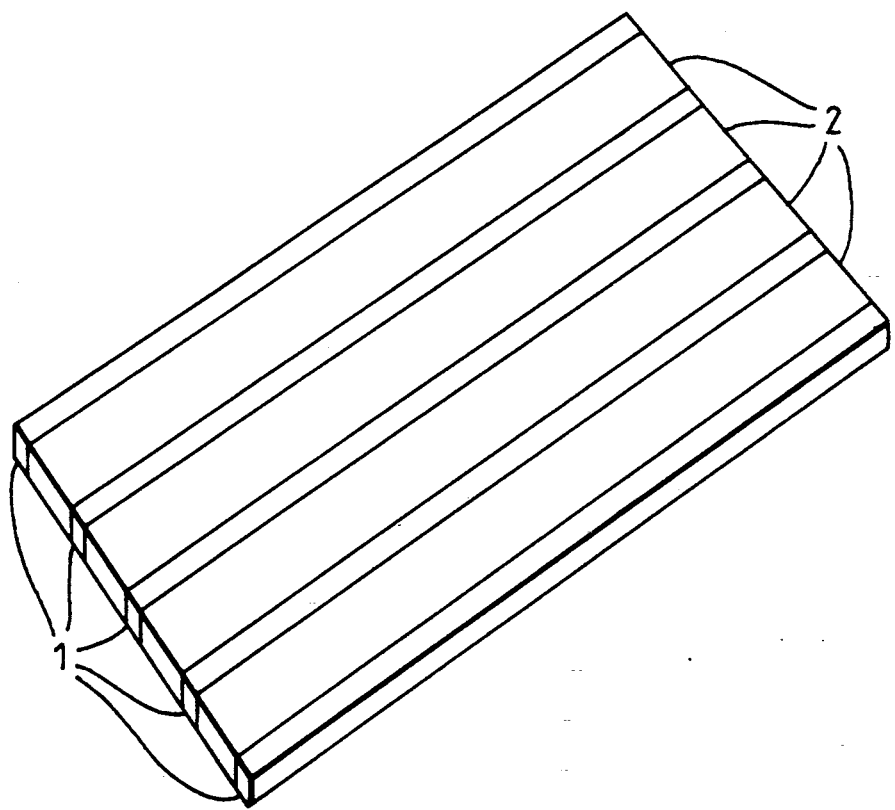
FIG. 1 is a schematic perspective view of a planar composite membrane of the invention showing the striations of interconnect and bands of electrolyte.

In FIG. 1, the composite membrane comprises a plurality of essentially parallel interconnect striations/stripes (1) which are contiguous with essentially parallel electrolyte bands (2). The membrane thus comprises an alternating arrangement of interconnect striations and electrolyte bands which extend between opposing edges of the membrane.

Figure 2:
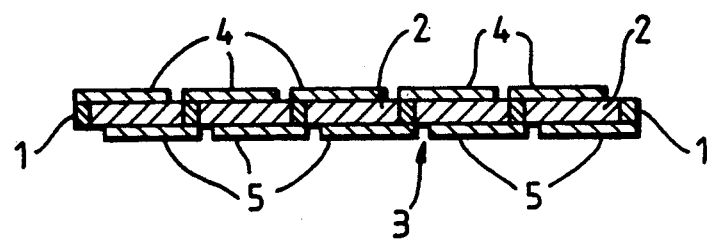
FIG. 2 is a schematic cross-sectional view of an electrochemical cell of the invention.

In FIG. 2, the electrochemical cell comprises a composite membrane (3) having a plurality of essentially parallel and alternating interconnect striations (1) and electrolyte bands (2). Essentially parallel bands of anodic electrode material (4) are arranged on one major face of the membrane and essentially parallel bands of cathodic electrode material (5) are arranged on the other major face of the membrane. Each anode and each cathode contact both an interconnect striation and an electrolyte band to the side of the interconnect striation without contacting the adjacent anodes/cathodes so arranged. Accordingly, each interconnect striation is contacted by an anode on one major face of the membrane and a cathode on the other, and each electrolyte band is likewise contacted by an anode and a cathode.

Figure 3:
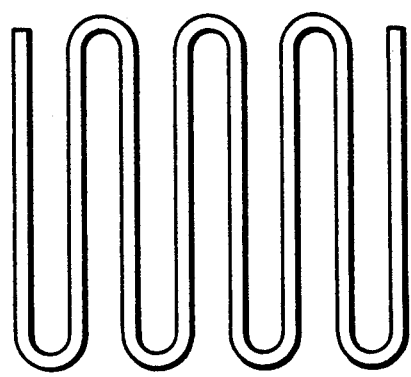
FIG. 3 is a schematic end view of an electrochemical cell of the invention which has a corrugated shape.

In FIG. 3, the electrochemical cell describes a corrugated shape. The various components of the electrochemical cell (not shown) have the form shown in FIG. 2. The interconnect striations, electrolyte bands and electrode bands extend laterally across the corrugated cell structure shown in FIG. 3 from the left hand side to the right hand side thereof.

Figure 4:
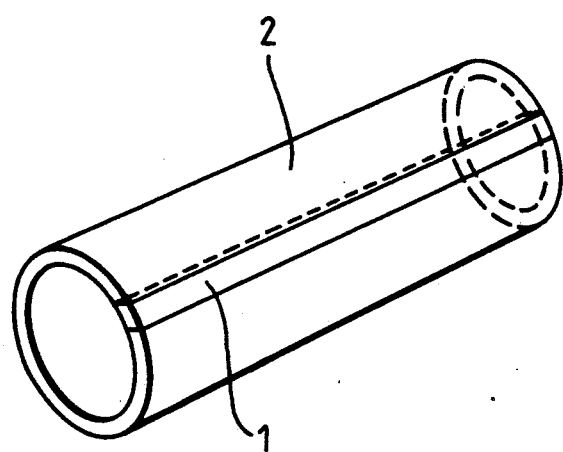
FIG. 4 is a schematic perspective view of a tubular composite membrane of the invention.

In FIG. 4, the composite membrane has the form of a tube. The tubular membrane comprises a band of electrolyte material (2) which extends along the whole length of the tube and for most of the circumference thereof, and a fine stripe of interconnect material (1) which extends along the whole length of the tube. Both the electrolyte band and the interconnect stripe traverse the thickness of the tubular membrane, and, in consequence, can be contacted on the inner and outer surfaces of the tubular membrane (i.e. the major faces of the membrane) by electrode components arrangeable thereon.

The present invention is now illustrated but not limited by the following Examples.

In all the following examples, zirconia powder stabilised with 8 mol % yttria and modified to sinter at 1500° C. was used as the electrolyte material. Modification of the zirconia powder was effected by calcining the powder in a furnace at a temperature of from 1400° to 1450° C. in order to grow the grains to about 1 micron. The calcined material was then milled in a bead mill to produce a fine powder.

EXAMPLE 1

Zirconia powder stabilised with 8 mol % yttria (HSY8 Daichi Kigenso; modified to sinter at 1500° C.) (the electrolyte material) was mixed with polyvinyl butyral and cyclohexanone in weight proportions 100/6/9 using a twin roll mill, to form a deformable electrolyte dough which was de-aired by pressing into a 1 mm thick sheet using 5 MPa pressure. This sheet was cut into strips 10 mm wide and the strips were assembled into an alternating electrolyte/interconnect dough layer with similarly prepared, 1 mm wide, dough strips of interconnect material. The interconnect material was Sr doped lanthanum chromite powder. Dough strips 10 mm wide and 0.3 mm thick comprising either particulate zirconia nickel cermet (i.e. the anodic electrode material) or Sr doped lanthanum manganite powder (i.e. the cathodic electrode material) were prepared in the same way as described above. The anode dough strips were laid down on one face of the electrolyte/interconnect dough layer and the cathode dough strips were laid down on the opposing face. The resulting dough trilayer was pressed and then calendered on a roll mill to form a precursor cell in the form of a thin tape of 0.2 mm thickness. This tape was wrapped around zirconia fibre boards to form a convoluted structure which was then heated to 90° C. to evaporate the solvent. The polymer binder was burned out by increasing the temperature at 1° C./minute to 550° C., and the resulting particulate assembly sintered at 1500° C. for 1 hour. The fibre boards were removed and the electrochemical cell retained the shape shown in FIG. 3.

EXAMPLE 2

This Example illustrates the preparation of a tubular composite membrane and electrochemical cell.

Zirconia powder stabilised with 8 mol % yttria (HSY8 Daichi Kigenso; modified to sinter at 1500° C.) (the electrolyte material) was mixed with polyvinyl butyral and cyclohexanone in weight proportions 60/5/7 using a twin roll mill, to form a deformable electrolyte dough which was de-aired by pressing into a 1 mm thick sheet using 5 MPa pressure. This sheet was cut into circular discs 13 mm in diameter, and a 40° segment of material was removed from each disc. The discs of electrolyte dough were then stacked in coaxial relation with the removed segments in line to form a rod shaped stack having a longitudinally extending open segment. An interconnect dough containing Ca doped lanthanum chromite powder (the interconnect material), polyvinyl butyral and cyclohexanone in weight proportions 60/5/7 was prepared on a twin roll mill. The interconnect dough was filled into the open segment to form a cylindrical rod which was then loaded into a ram extruder and extruded to give a tubular precursor membrane having an outer diameter of 2.5 mm and a wall thickness of 250 μm.

The tube was then dried, heated at 1° C./minute to 500° C. in order to burn out the polymer binder and finally heated at 1500° C. for 1 hour to sinter the particulate electrolyte and interconnect materials. The resulting tubular composite membrane was mainly composed of electrolyte material and comprised a 1 mm wide stripe of interconnect material which extended along the length of the tube. The tube had the form shown in FIG. 4.

Electrode components were then applied to the inner and outer surfaces of the tubular composite membrane by coating. A first coating composition prepared by dispersing lanthanum strontium manganite powder (a cathodic electrode material) in a polymer/solvent (cellulose/terpineol) liquid vehicle was poured down the inside of the tubular composite membrane. Any excess of the coating composition was drained away to leave a coating of the particulate cathode material on the inner surface of the tube. A second coating composition prepared by dispersing nickel oxide and stabilised zirconia powder (an anodic electrode material) in a polymer/solvent (cellulose/terpineol) liquid vehicle was painted on the outer surface of the tube in the region of the electrolyte domain, care being taken to avoid the interconnect stripe. The coated tube was allowed to dry and then heated at 1° C./minute to 500° C. in order to burn out the cellulose polymer. Finally, the coated tube was fired at 1200° C. to sinter the electrodes.

A plurality of electrode coated tubes prepared as described above can be assembled in juxtaposition to form an electrochemical cell in which the exposed surface of the interconnect stripe of one composite membrane (i.e. the surface which was not coated with the anode) contacts an anode coated on the outer surface of an adjacent composite membrane. In such an electrochemical cell, the interconnect stripe of a given composite membrane makes contact with the cathode coated on the inner surface of that membrane and an anode coated on the outer surface of an adjacent membrane.

EXAMPLE 3

This Example illustrates the preparation of a tubular composite membrane.

Zirconia powder stabilised with 8 mol yttria (HSY8 Daichi Kigenso; modified to sinter at 1500° C.) (the electrolyte material) was mixed with polyvinyl butyral and cyclohexanone in weight proportions 60/5/7 using a twin roll mill, to form a deformable electrolyte dough which was de-aired by pressing into a 1 mm thick sheet using 5 MPa pressure. This sheet was then cut into circular discs 13 mm in diameter. A sheet of interconnect dough containing Ca doped lanthanum chromite powder, polyvinyl butyral and cyclohexanone in weight proportions 60/5/7 was similarly prepared. The sheet of interconnect dough was then cut into circular discs 13 mm in diameter, and these discs were then cut into 40° segments. The discs of electrolyte dough and the segments of interconnect dough were then assembled, alternately, into a rod shaped stack in which the segments of interconnect dough were in line and interposed between the discs of electrolyte dough. The rod shaped stack was then loaded into a ram extruder and extruded to give a tubular precursor membrane having an outer diameter of 2.5 mm and a wall thickness of 250 μm.

The tube was then dried, heated at 1° C./minute to 500° C. in order to burn out the polymer binder and finally heated at 1500° C. for 1 hour to sinter the particulate electrolyte and interconnect materials. The resulting tubular composite membrane was mainly composed of electrolyte material and comprised a 1 mm wide intermittent stripe of interconnect material which extended along the length of the tube.

EXAMPLE 4

Zirconia powder stabilised with 8 mol % yttria (HSY8 Daichi Kigenso; modified to sinter at 1500° C.) (the electrolyte material) was mixed with polyvinyl butyral and cyclohexanone in weight proportions 100/6/9 using a twin roll mill, to form a deformable electrolyte dough which was de-aired by pressing into a 1 mm thick sheet using 5 MPa pressure. This sheet was cut into a rectangular shape and 1 mm holes were then punched into the sheet. A similarly prepared sheet of interconnect dough containing Sr doped lanthanum chromite powder as the interconnect material was cut into circular pieces 1 mm in diameter. The holes in the sheet of electrolyte dough were then filled with the 1 mm diameter pieces of interconnect dough. The resulting dough layer was then calendered on a roll mill to form a precursor membrane of 0.2 mm thickness. The membrane was then heated to 90° C. to evaporate the solvent, heated at 1° C./minute to 550° C. to burn out the polymer binder and finally heated at 1500° C. for 1 hour to sinter the particulate electrolyte and interconnect materials. The final composite membrane was a generally planar sheet composed mainly of electrolyte material with intermittent stripes of interconnect material.

EXAMPLE 5

Zirconia powder stabilised with 8 mol % yttria (HSY8 Daichi Kigenso; modified to sinter at 1500° C.) (the electrolyte material) was mixed with polyvinyl butyral and cyclohexanone in weight proportions 100/6/9 using a twin roll mill, to form a deformable electrolyte dough which was de-aired by pressing into a 1 mm thick sheet using 5 MPa pressure. This sheet was cut into a rectangular shape. An interconnect dough containing Sr doped lanthanum chromite powder as the interconnect material, polyvinyl butyral and cyclohexanone in weight proportions 100/6/9 was prepared using a twin roll mill. The interconnect dough was then extruded into a fibre and the resulting fibre was sewn through the sheet of electrolyte dough. The resulting dough layer was then calendered on a roll mill to form a precursor membrane of 0.2 mm thickness. The membrane was then heated to 90° C. to evaporate the solvent, heated at 1° C./minute to 550° C. to burn out the polymer binder and finally heated at 1500° C. for 1 hour to sinter the particulate electrolyte and interconnect materials. The final composite membrane was a generally planar sheet composed mainly of electrolyte material with stripes of interconnect material passing along and through the electrolyte material.

I claim:

1. A composite membrane comprising at least one domain of an electrolyte material and at least one domain of an electronically conducting interconnect material, said electrolyte domain and said interconnect domain traversing the thickness of the membrane so that the membrane comprises contact surfaces for the electrolyte domain and the interconnect domain on both major faces thereof.

2. A composite membrane as claimed in claim 1 characterised in that it comprises a plurality of domains formed from the electrolyte material and a plurality of domains formed from the interconnect material.

3. A composite membrane as claimed in claim 2 characterised in that it comprises an alternating arrangement of electrolyte bands and interconnect striations which extend between opposing edges of the membrane.

4. A composite membrane as claimed in any one of the preceding claims characterised in that it has a corrugated or spiral shape.

5. A composite membrane as claimed in claim 1 or claim 2 characterised in that it has a tubular shape.

6. A composite membrane as claimed in claim 5 characterised in that it comprises one or more bands of electrolyte material and one or more striations of interconnect material which extend along the length of the tube.

7. An electrochemical cell comprising:
   (a) at least one composite membrane having at least one domain of an electrolyte material and at least one domain of an electronically conducting interconnect material, which domains traverse the thickness of the membrane;
   (b) one or more anodes arranged on one major face of the composite membrane; and
   (c) one or more cathodes arranged on the other major face of the composite membrane, the arrangement of the components in the cell being such that the electrolyte domain and the interconnect domain make contact with both an anode and a cathode, and the anode and the cathode make contact with both an electrolyte domain and an interconnect domain.

8. An electrochemical cell as claimed in claim 7 characterised in that it comprises:
   (a) at least one composite membrane having a plurality of domains formed from the electrolyte material and a plurality of domains formed from the interconnect material;
   (b) a plurality of anodes arranged on one major face of each membrane; and
   (c) a plurality of cathodes arranged on the other major face of each membrane.

9. An electrochemical cell as claimed in claim 8 characterised in that it comprises:
   (a) at least one composite membrane comprising an alternating arrangement of electrolyte bands and interconnect striations which extend between the opposing edges of the membrane;
   (b) a plurality of anode bands arranged on one major face of each membrane; and
   (c) a plurality of cathode bands arranged on the other major face of each membrane.

10. An electrochemical cell as claimed in claim 7 characterised in that it has a corrugated or spiral shape.

11. An electrochemical cell as claimed in claim 7 or claim 8 characterised in that it comprises:
    (a) a tubular composite membrane;
    (b) one or more anodes arranged on one of either the inner or outer surface of the tubular composite membrane; and
    (c) one or more cathodes arranged on the other of either the inner or outer surface of the tubular composite membrane.

12. An electrochemical cell as claimed in claim 11 characterised in that the composite membrane comprises one or more bands of electrolyte material and one or more striations of interconnect material which extend along the length of the tube.

13. A solid oxide fuel cell comprising one or more of the composite membranes claimed in claim 1.

14. A solid oxide fuel cell comprising one or more of the electrochemical cells claimed in claim 7.

15. A method of preparing a composite membrane as claimed in claim 1 which method comprises the steps of:
    (1) separately dispersing a particulate electrolyte material and a particulate interconnect material in a polymer based binder to form mouldable electrolyte and interconnect doughs;
    (2) forming the electrolyte and interconnect doughs into a cohesive precursor membrane comprising one or more domains of the particulate electrolyte material and one or more domains of the particulate interconnect material each bound together by the polymer based binder;
    (3) removing the polymer based binder; and
    (4) sintering the particulate electrolyte and interconnect materials to form the composite membrane.

* * * * *